United States Patent
Hakimuddin

(10) Patent No.: US 10,048,336 B2
(45) Date of Patent: Aug. 14, 2018

(54) TRI-AXIAL NMR TEST INSTRUMENT

(71) Applicant: Saudi Arabian Oil Company, Dhahran (SA)

(72) Inventor: Mustafa Hakimuddin, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 789 days.

(21) Appl. No.: 14/018,557

(22) Filed: Sep. 5, 2013

(65) Prior Publication Data

US 2015/0061669 A1 Mar. 5, 2015

(51) Int. Cl.
| | |
|---|---|
| G01R 33/44 | (2006.01) |
| G01R 33/28 | (2006.01) |
| G01V 3/14 | (2006.01) |
| G01N 24/08 | (2006.01) |
| G01V 3/32 | (2006.01) |
| G01R 33/30 | (2006.01) |
| G01N 33/28 | (2006.01) |
| G01N 3/10 | (2006.01) |

(52) U.S. Cl.
CPC ........... *G01R 33/44* (2013.01); *G01N 24/081* (2013.01); *G01N 33/28* (2013.01); *G01R 33/28* (2013.01); *G01R 33/305* (2013.01); *G01V 3/14* (2013.01); *G01V 3/32* (2013.01); *G01N 3/10* (2013.01)

(58) Field of Classification Search
CPC ...... G01R 33/44; G01R 33/305; G01R 33/28; G01N 33/28; G01N 24/081; G01N 3/10; G01V 3/32; G01V 3/14
See application file for complete search history.

(56) References Cited

U.S. PATENT DOCUMENTS

| | | | |
|---|---|---|---|
| 5,134,271 A | 7/1992 | Sondergeld et al. | |
| 5,159,828 A | 11/1992 | Steiger et al. | |
| 5,275,063 A | 1/1994 | Steiger et al. | |
| 5,325,723 A * | 7/1994 | Meadows | G01N 3/10 |
| | | | 100/106 |
| 6,609,067 B2 | 8/2003 | Tare et al. | |
| 7,042,802 B2 | 5/2006 | Sinha | |
| 7,274,992 B2 | 9/2007 | Dewhurst et al. | |
| 7,472,022 B2 | 12/2008 | Birchwood | |
| 7,555,414 B2 | 6/2009 | Calhoun et al. | |

(Continued)

FOREIGN PATENT DOCUMENTS

| | | |
|---|---|---|
| EP | 0372636 A2 | 6/1990 |
| SU | 1508147 A1 | 9/1989 |

OTHER PUBLICATIONS

Wang, Z., Gelius, L.-J. and Kong, F.-N. (2009), Simultaneous core sample measurements of elastic properties and resistivity at reservoir conditions employing a modified triaxial cell—a feasibility study. Geophysical Prospecting, 57: 1009-1026. doi: 10.1111/j.1365-2478.2009.00792.x.*

(Continued)

*Primary Examiner* — David M Gray
*Assistant Examiner* — Laura Roth
(74) *Attorney, Agent, or Firm* — Bracewell LLP; Constance G. Rhebergen; Linda L. Morgan

(57) ABSTRACT

The invention provides a tri-axial nuclear magnetic resonance apparatus for testing of petro-physical properties and gathering of geo-mechanical information and methods of using the same. The tri-axial nuclear magnetic resonance apparatus includes a tri-axial load frame encasing a tri-axial load cell that includes a tri-axial sample holder, at least one electrical sensor, at least one acoustic sensor, and a nuclear magnetic resonance instrument.

18 Claims, 1 Drawing Sheet

(56) References Cited

U.S. PATENT DOCUMENTS

| | | | |
|---|---|---|---|
| 8,301,383 | B2 | 10/2012 | Birchwood et al. |
| 8,443,661 | B1 | 5/2013 | Bi |
| 2004/0202401 | A1* | 10/2004 | Berg .................. G01V 11/00 385/12 |
| 2005/0150273 | A1* | 7/2005 | Potter .................. G01N 3/10 73/38 |
| 2011/0050223 | A1 | 3/2011 | Balcom et al. |
| 2015/0061670 | A1* | 3/2015 | Fordham .............. G01N 24/081 324/309 |

OTHER PUBLICATIONS

Chryssanthakis P., Rose E., Westerdahl H., Rhett D. and Pederson S. 1999. High temperature triaxial tests with ultrasonicmeasurements on Ekofisk chalk. RockMechanics for Industry. Proceedings of the 37th Rock Mechanics Symposium, [Retrieved from the Internet] <https://www.onepetro.org/conference-paper/ARMA-99/0373> pp. 373-379.*

PCT Communication Relating to the Results of the Partial International Searching Authority; dated Nov. 18, 2014; International Application No. PCT/US2014/051418; International File Date: Aug. 18, 2014.

Han, H., et al.; High Pressure Magnetic Resonance Imaging With Metallic Vessels; Journal of Magnetic Resonance; Sep. 10, 2011; pp. 90-97; vol. 213; Elsevier, Inc.

Skagius, K., et al.; Diffusivity Measurements and Electrical Resistivity Measurements in Rock Samples Under Mechanical Stress; Water Resources Research; Apr. 4, 1986; pp. 570-580; vol. 22, No. 4.

\* cited by examiner

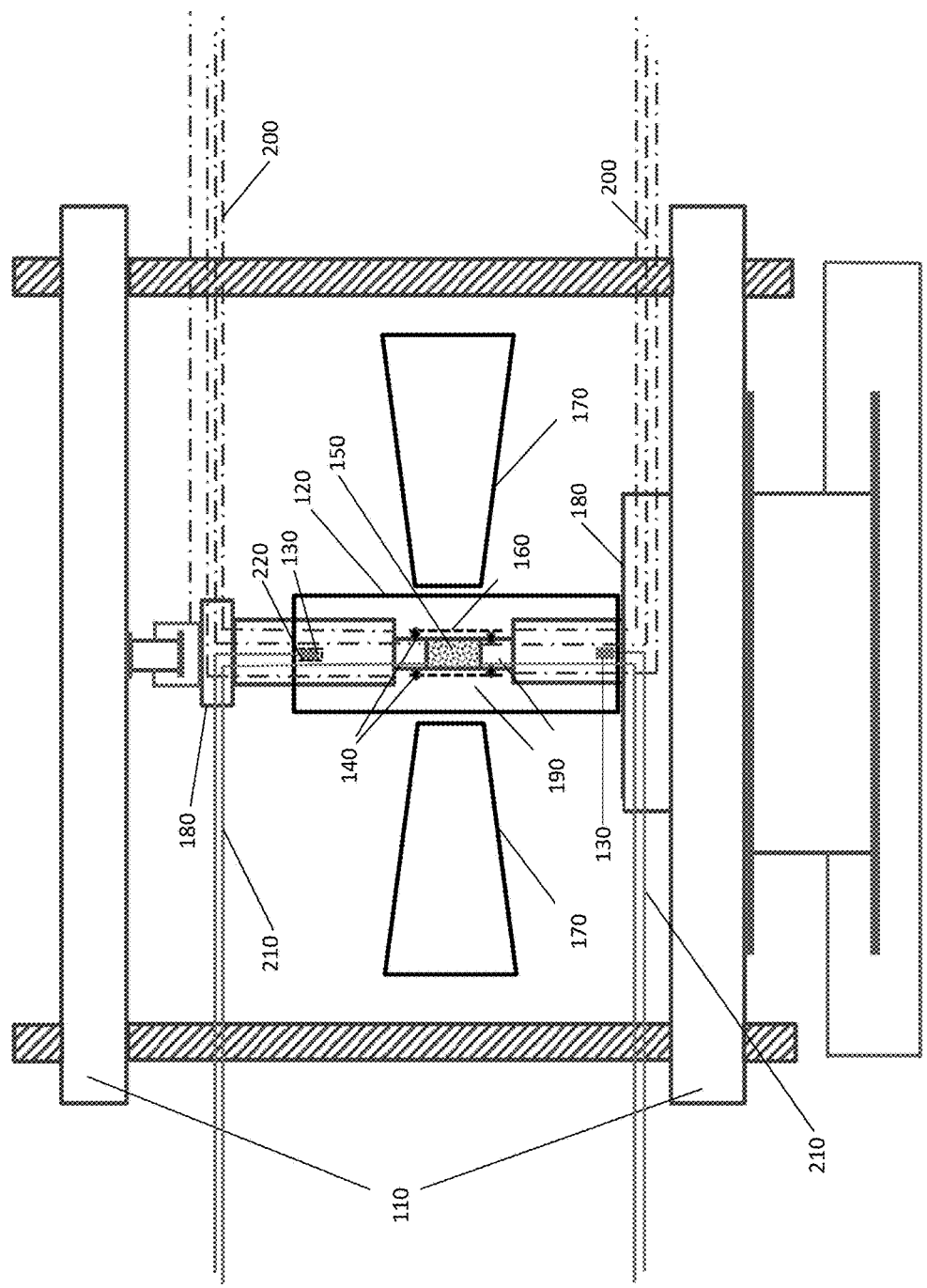

TRI-AXIAL NMR TEST INSTRUMENT

FIELD OF THE INVENTION

Generally, this invention relates to a tri-axial NMR test apparatus. The tri-axial NMR test apparatus is capable of assessing petro-physical properties and geomechanical properties.

BACKGROUND OF THE INVENTION

The current petroleum exploration and production environment, with emphasis on maximizing reservoir production with enhanced oil recovery ("EOR") and intense competition for safely exploiting the unconventional hydrocarbon reservoir, dictates improvement in all phases of reservoir development cycles. Since the inception of hydrocarbon production, accuracy in reserve estimation, maximum achievable recovery estimation, and rate of production estimation, are basic questions that should be answered to assess oil recovery efforts. In the last thirty years or so, the industry has made significant strides in improving the means for providing answers to these questions. However, with many of the world's reservoirs at peak production and unconventional drilling methods taking the forefront, the need for improved data accuracy and delivery time to assist in decision making has gained importance. A need exists for accurate, cost effective assessment of reserve estimation, maximum achievable recovery, and potential rate of production that can be conducted in a timely fashion.

Moreover, in the oil industry it is imperative to evaluate reservoir rock and fluid interactions at formation temperature and pressure conditions. As reservoir fluids are produced, temperature, pressure, fluid phase, fluid composition, and rock behavior is constantly changing due to changes in temperature, pressure, and other parameters. These changes need to be modeled, and their effect on reservoir production needs to be understood. For this purpose, proper test equipment, test design, and various sensor technologies needs to be employed, to generate data that could predict reservoir behavior from exploration to abandonment. Furthermore, the test techniques and test equipment need to be sophisticated so as to properly analyze unconventional reservoirs, such as shale gas, tight gas sand (TGS), heavy oil, tar sand, hydrates, and depleted enhanced oil recovery reservoirs. Successful design and implementation of any unconventional reservoir or FOR mechanism (such as water, steam, chemical, thermal, and biological mechanisms) must be studied under a correct set of reservoir conditions to obtain the desired results from an EOR treatment analysis.

Furthermore, the test data collected on reservoir retrieved core and fluid samples must have attributes to mimic a broader set of data that is continuously acquired during logging, well testing, and seismic data gathering. The current NMR setups available lack the ability to generate data under reservoir conditions.

SUMMARY

In one aspect, the invention provides a tri-axial nuclear magnetic resonance apparatus for testing of petro-physical properties and gathering of geo-mechanical information. The tri-axial nuclear magnetic resonance apparatus includes a tri-axial load frame encasing a tri-axial load cell having a tri-axial sample holder and at least one space surrounding the tri-axial sample holder, at least one end cap operable to contact the tri-axial load cell, at least one electrical sensor, at least one acoustic sensor, and a nuclear magnetic resonance instrument.

In another aspect, the invention provides a method of using the tri-axial nuclear magnetic resonance apparatus. The method includes obtaining a sample from a reservoir and loading the tri-axial sample holder in the tri-axial load cell to create a loaded tri-axial load cell. The loaded tri-axial load cell is then placed in contact with at least one end cap of the tri-axial nuclear magnetic resonance apparatus. A tri-axial pressure is then applied by providing fluid flow through the at least one end cap to the at least one space surrounding the tri-axial sample holder. Tri-axial pressures can include any combination of the following pressures: radial pressure, axial pressure, confining pressure, and pore pressure. A temperature control fluid is then circulated around the loaded tri-axial sample holder by providing the temperature control fluid through the at least one end cap to the at least one space surrounding the tri-axial sample holder to maintain the temperature of the tri-axial sample holder during analysis. A test fluid is then provided through the at least one end cap to the loaded sample holder. A time dependent slice nuclear magnetic resonance scan of the sample is performed using the nuclear magnetic resonance instrument. Electrical analysis of the sample using the at least one electrical sensor and acoustical analysis of the sample using the at least one acoustic sensor are also performed.

BRIEF DESCRIPTION OF THE DRAWINGS

The FIGURE is a tri-axial NMR apparatus in accordance with an embodiment of the present invention.

DETAILED DESCRIPTION OF THE INVENTION

Although the following detailed description contains many specific details for purposes of illustration, it is understood that one of ordinary skill in the art will appreciate that many examples, variations and alterations to the following details are within the scope and spirit of the invention. Accordingly, the exemplary embodiments of the invention described herein and provided in the appended FIGURE are set forth without any loss of generality, and without imposing limitations, on the claimed invention.

The invention generally relates to core analysis, fluid analysis, petro-physical analysis and phase behavior evaluation of hydrocarbon reservoirs under tri-axial stress conditions with pore pressure. The tri-axial NMR apparatus described herein perform multiple tests on a sample at the same time and also integrate the data collected related to various sample properties. The apparatus allows for reservoir modeling. For example, when collecting acoustic sonic) data during NMR measurements, the apparatus will provide information regarding the mechanical stress changes on the sample not only as a function of pressure change, but also as the formation fluid changes. This information is directly used during seismic monitoring of reservoir production and for tuning simulation models for production profiles.

In one aspect, the invention provides the tri-axial nuclear magnetic resonance apparatus for testing of petro-physical properties and gathering of geo-mechanical information. The tri-axial nuclear magnetic resonance apparatus includes the tri-axial load frame encasing the tri-axial load cell having the tri-axial sample holder and the at least one space surrounding the tri-axial sample holder, at least one end cap operable to contact the tri-axial load cell, at least one electrical sensor, at least one acoustic sensor, and the nuclear magnetic resonance instrument.

The tri-axial load cell includes a tri-axial sample holder. The tri-axial sample holder can be made of any material acceptable for a tri-axial sample holder. In general, the tri-axial sample holder will either have no NMR signature, or a known NMR signature. In preferred embodiments, the tri-axial sample holder is made of TORLON® (available from Solvay Plastics). TORLON® is preferred as it has a very high pressure and temperature rating and is "invisible" to the NMR. In some embodiments, the design of the tri-axial sample holder is such that the tri-axial sample holder is free of any connection on the outer face of the tri-axial sample holder, hence providing higher hoop strength for higher confining pressures. The tri-axial sample holder is designed such that it has no orifices for fluid or electrical connection on the outer surface. The fluid for both confining pressure and pore pressure is provided via the at least one end cap on the tri-axial load cell to the at least one space surrounding the tri-axial sample holder. In some embodiments, there are two end caps. The end caps can be floating end caps that provide accommodation of various lengths of samples within the same tri-axial sample holder. This design has additional benefits of reducing the wall thickness of test vessel, hence allowing a larger diameter sample to be used. In some embodiments, the tri-axial sample holder is in the shape of a cylinder. In further embodiments, the diameter of the cylinder can be from about 0.1 inches to about 4 inches. The length of the cylinder can be from about 0.1 inches to about 20.0 inches. In general, the tri-axial sample holder is capable of withstanding stresses associated with generating fracture and/or applying axial stress (i.e., stresses found in reservoirs).

The tri-axial load frame serves to encase the components of the apparatus. In general, the tri-axial load frame should either have no NMR signature, or a known NMR signature. In some embodiments, the tri-axial load frame is made from titanium with an additional coating for increasing inertness to NMR and to handle corrosive chemicals, acids, and industrial solvents that may be used during testing. Such chemicals include toluene, methanol, chloroform, carbon dioxide (liquid and/or gas), methane, water, xylene, hydrochloric acid, and acetic acid. In further embodiments, the tri-axial load frame is expandable to accommodate longer samples. In some embodiments, the tri-axial load frame also encases deformation measurement devices such as a linear variable differential transformer, a strain gauge, and an infrared or acoustic displacement system to measure static mechanical properties of the sample.

The tri-axial load cell can provide axial stress independent of confining and pore pressure. The tri-axial load cell is connected to a pump and pressure gauge for applying and monitoring the axial stress on the sample loaded into the tri-axial sample holder. The tri-axial load cell can be used to initiate fractures in a sample to study fracture mechanics with fluid transport. In some embodiments, the tri-axial load cell is made of coated titanium.

The tri-axial load cell further includes at least one end cap. In some embodiments, there are two end caps. The end caps have pore lines to allow for fluid flow. The pore lines allow for fluid flow into the at least one space surrounding the tri-axial sample holder and into the tri-axial sample holder. Fluid flow can be provided via the pore lines using injection, application, or any other supply mechanism known to those of skill in the art. In some embodiments, the end caps have three pore lines. In some embodiments, the end caps are made of aluminum or TORLON®. In further embodiments, the end caps are embedded with a conductor that allows for current flow. Any acceptable conductor can be used. In preferred embodiments, the conductor is selected from gold, platinum, or aluminum. The end caps further include one or more cavities for housing the at least one acoustic sensor. In further embodiments, the end caps are floating such that they can accommodate a variety of sample sizes.

The tri-axial load cell further includes pore pressure lines, acoustic sensor feeds, and electrical sensor feeds. The pore pressure lines, acoustic sensor feeds, and electrical sensor feeds can be located on or in the end caps.

In further embodiments, the tri-axial load cell is equipped with a piston separator to perform various PVT analyses, such as viscosity, compressibility, constant composition expansion, wax, asphaltene, and hydrate formation. In one embodiment, if the sample is a fluid. and a specific NMR. probe is used, then it is possible to detect asphaltene as function of carbon-13. It is also possible to identify hydrate structure, which is a desirable aspect of hydrate production and mitigating flow assurance, as well bore stability issues related to wax, asphaltene, hydrate, and salt crystallization.

In some embodiments, the at least one electrical sensor is a resistivity probe which provides electrical property measurements at the same time as other properties are measured. This assists in integration of various lab and field data for both rock and fluids of the reservoir. In some embodiments, the fluid and associated pore line on the ends of the tri-axial sample holder can be used to measure electrical response. In instances of a non-conductive fluid, non-magnetic conductors may be installed on the sample during sample preparation for the purpose of electrical property measurements. In some embodiments, an impedance analyzer can be used to assess the voltage, current, phase, and resistivity of the sample.

In some embodiments, the acoustic sensor is an acoustic transducer with variable frequency and mode (e.g., shear, longitudinal). Various mode transducers, along with variable frequency, allow the analysis to target specific pore size, grain size, or fluid components. The acoustic transducer measures various dynamic properties of the sample under tri-axial conditions with accurate fluid saturation and an easy path for log data integration. In some embodiments, the at least one acoustic sensor is operable to function as a transmitter and a receiver. Among the acoustic properties that may be measured include the P-wave (longitudinal) and S-wave (shear) at 180, 90, and 45 degree angles both in transmission and reflection mode, and travel time, along with the complete frequency spectra. Dual mode transducers may be selected based on the sample size and test procedure, with frequency ranges from lower KHz used in logging tools for bulk properties of rock and fluid to higher frequency ranges in order to investigate detailed diffusion patterns and pore geometries with the test samples. Many such transducers are readily available. Additionally, a person of skill in the art may also specially design a transducer based on specific sample parameters under investigation.

By having the capability of performing acoustic measurements with various modes with the tri-axial NMR apparatus, there is increased understanding of formation damage due to sand migration, and formation damage due to wax and asphaltene drop out as temperature and pressure changes. Such measurements will also assist in assessment of provided fluid interaction with the rock matrix, especially in chemical EOR, as the tri-axial capability helps mimic the stress regime in a given reservoir more so than the conventional hydrostatic test vessels currently available. The additional acoustic and resistivity measurements also provide a suitable method for calibrating field log data before and after EOR on a specific field.

The NMR instrument can be any NMR appropriate for these particular applications. In general, a large bore NMR with appropriate signal to noise ratio, and signals received with minimum time delay, is acceptable. in general, the NMR should have the gradient and appropriate bore diameter for the tri-axial load cell. A NMR with a proper combination of gradient and reduced time delay will provide not only a saturation profile between the hydrocarbon and non-hydrocarbon fluids, but will also identify bound and free water, assist in differentiating between oil and kerogen, and may assist in differentiating between kerogen hydrocarbon gases and asphaltene.

The NMR can have capability to perform both whole and thin slice scanning. The capability of performing focused NMR scanning on a smaller area will provide more detail features of the sample. The technique will be used to measure the permeability of unconventional tight reservoir and will be able to differentiate between matrix permeability, fracture permeability, and diffusivity of various fluids. A fluid will be provided to one face of the sample and time dependent slice NMR scanning will be performed to see the movement and shape of the front providing valuable transport behavior of the reservoir sample. In some embodiments, the tri-axial NMR apparatus will be equipped with a controlled positioning device, or cell mobilizer, to provide accurate and repeatable slice location. This can be achieved for a shorter sample by moving a window between the NMR borehole and test vessels and for longer sample, the whole NMR can be mobilized to provide slice scans. The NMR has the capability to perform NMR scans as 0.1 mm slice to 152.4 mm (6.0 inch) slice, for 360 degrees. Additionally, the NMR can have a variable magnetic field and frequency ranging from KHz to MHz. This range will assist in focusing on various rock and fluid constituent in detail.

The NMR can also have a variable probe for hydrogen, carbon-13, sodium, and other components likely to occur in a reservoir. Such a probe will focus testing on various components of the rock fabric and fluids. For example, a sodium probe scan along with a hydrogen probe scan will amplify the difference between free water and bound water, as well as provide information about the salinity of the formation. Similarly, a carbon-13 probe can help in identifying maturity and type of kerogen in a sample.

In further embodiments, the tri-axial nuclear magnetic resonance apparatus has pore-pressure capability which allows for raising fluid pressure to reservoir conditions. Additionally, this setup allows for measurement of permeability in both steady state and un-steady state method with dead or live fluids. Steady state is a relative permeability test where two or more fluids are provided simultaneously at one end of a cylindrical plug sample of reservoir rock and the change in sample fluid saturation is monitored as a function of fluid produced on the other end to mimic reservoir injection. Un-steady state is a test where one fluid is provided in the rock plug sample in the presence of a second fluid inside the sample and production of both fluids is monitored on the other end of the sample. This mimics how the reservoirs were formed initially and is also the mechanism of primary oil production. Dead fluid is fluid with no, or a very small amount of, gas. Live fluid is fluid with gas in it at the same chemical composition as found in a given hydrocarbon reservoir.

In further embodiments, the tri-axial nuclear magnetic resonance apparatus can also include one or more semi-permeable membranes for analyzing capillary pressure and wettability measurements. In one configuration of the instrument setup, one or more porous semi-permeable membranes can be incorporated to perform capillary pressure and wettability analysis of a reservoir sample under tri-axial test conditions with NMR saturation and other measurements. There are many advantages of performing this analysis, beyond the obvious one of data integration. One major advantage is to tune various empirical equations used in simulation of reservoirs with real data.

In further embodiments, the tri-axial nuclear magnetic resonance apparatus can also include feeds to a second NMR for injection and production fluid evaluation under stress conditions. This has added value for performing detailed research to evaluate various nano technology fluids and other phase behavior attributes of reservoir or injected fluids.

The tri-axial nuclear magnetic resonance apparatus includes a pressurized fluid circulation system to maintain temperature and pressure during testing.

The tri-axial nuclear magnetic resonance apparatus further includes high pressure pumps for providing various stresses for sample and fluid flow.

In some embodiments, the tri-axial nuclear magnetic resonance apparatus includes a sample strain measurement system or displacement measurement device. Such a sample strain measurement system or displacement measurement device could be electrical, infrared, acoustical, or any other kind based on sample and test condition requirements. The advantage of performing strain measurements on a reservoir rock sample is that it relates to mechanical strength and formation damage issues. The advantage of performing strain measurements on a fluid sample is that it relates to production profiles and flow assurance issues.

The tri-axial nuclear magnetic resonance apparatus can also include a high pressure densitometer and viscosity meter at the injection and production ends for transport behavior evaluation. These types of meters provide valuable information about fluid property change during a core sample test. For instance, these tests may show that at different pressure and flow rates the possibility of emulsification of injected fluid and the rock matrix.

In further embodiments, the tri-axial nuclear magnetic resonance apparatus includes an acoustic separator on the production end for production measurements. Acoustic separators are known by persons of skill in the art. Such persons could readily select an appropriate acoustic separator for use in this invention.

In further embodiments, the tri-axial nuclear magnetic resonance apparatus includes a cylinder and fluid rocking system for live fluid injection. Cylinder and fluid rocking systems are known by persons of skill in the art. Such persons could readily select an appropriate cylinder and fluid rocking systems for use in this invention.

In further embodiments, the tri-axial nuclear magnetic resonance apparatus includes sensitive pressure sensors for various sample and fluid pressure monitoring. Sensitive pressure sensors are known by persons of skill in the art. Such persons could readily select an appropriate sensitive pressure sensor for use in this invention.

The FIGURE shows a tri-axial NMR apparatus according to an embodiment of the invention. This embodiment of the apparatus has tri-axial load frame 110. The apparatus further includes tri-axial load cell 120, NMR apparatus 170, end caps 180, acoustic sensors 130, electrical sensors 140, and tri-axial sample holder 150. Optionally, isolation jacket 160 may be added to surround the tri-axial sample holder. Additionally, shown are spaces 190 surrounding the tri-axial sample holder.

In another aspect, the invention provides a method of using the tri-axial nuclear magnetic resonance apparatus. The method includes obtaining a sample from a reservoir and loading the tri-axial sample holder in the tri-axial load cell to create a loaded tri-axial load cell. The loaded tri-axial load cell is then placed in contact with at least one end cap of the tri-axial nuclear magnetic resonance apparatus. A tri-axial pressure is then applied to the tri-axial load cell through the at least one end cap to the at least one space surrounding the tri-axial sample holder. A temperature control fluid is then circulated around the loaded tri-axial sample holder by providing the temperature control fluid through the at least one end cap to the at least one space surrounding the tri-axial sample holder to maintain the temperature of the tri-axial sample holder during analysis. A test fluid is then provided to the loaded tri-axial sample holder through the at least one end cap. A time dependent slice nuclear magnetic resonance scan of the sample is performed using the nuclear magnetic resonance instrument. Electrical analysis of the sample using the at least one electrical sensor and acoustical analysis of the sample using the at least one acoustic sensor are also performed.

The samples can be obtained from any reservoir. Exemplary reservoirs from which the sample can be obtained include unconventional reservoirs, such as shale gas, tight gas sand (TGS), heavy oil, tar sand, hydrates and depleted enhanced oil recovery reservoirs. The samples used for analysis can be a native sample or a clean sample. The term native sample means a reservoir rock plug sample that has been drilled and retrieved from reservoir and installed in the tri-axial sample holder without any alternation. The term clean sample means a sample that, after having been retrieved from a reservoir, has gone through various processes to remove all fluids and associated solids (such as salt, wax, and asphaltene).

Tri-axial pressures can include any combination of the following pressures: radial pressure, axial pressure, confining pressure, and pore pressure. In sonic embodiments, the radial pressure ranges from about 1 psi to about 30,000 psi, axial pressure ranges from about 1 psi to about 500,000 psi, pore pressure ranges from about 1 psi and 30,000 psi, and confining pressure ranges from about 1 psi and 31,000 psi. The pore pressure for the sample should be at least about 100 psi less than the confining and axial pressures. in general, the pressures are selected such that they mimic conditions of the reservoir being studied.

During analysis, the temperature of the tri-axial sample holder can be controlled to mimic conditions of the reservoir being studied. In some embodiments, the temperature can be controlled using a temperature control fluid. Acceptable temperature control fluids include any known temperature control fluids that have a minimum known, or no, effect, on the NMR signal. In some embodiments, the tri-axial sample holder is maintained at a temperature of between about −20° C. and 350° C. In general, the temperature is selected based on the temperature conditions in the reservoir being studied.

The test fluid provided to the loaded tri-axial sample holder through the at least one end cap includes a variety of fluids. "Provided" indicates that the test fluid is injected, applied, or otherwise supplied to the tri-axial sample holder. For instance, solvents such as toluene, methanol, chloroform, xylene, water, and carbon dioxide can be provided for leaching of hydrocarbons and salts. Acids of varying concentrations can be provided for cleaning and simulations. Hydrocarbon liquids, gasses, and brine solutions can be provided for flow capacity measurements. Wettability EOR chemicals can be provided for simulations. Fracturing fluids with propants can be provided for simulations. in some embodiments, the test fluid is a dead fluid. In other embodiments, the test fluid is a live fluid.

In some embodiments, the time dependent slice nuclear magnetic resonance scan of the sample measures nuclear magnetic frequencies from about 0.1 KHz to 20 MHz. The frequency will be selected based on the type of sample being assessed and the parameters being studied. For example, for a homogenous single pore type sample with low viscosity fluid (0.5 to 2.0 cP viscosity), a 2 MHz nuclear magnetic frequency may be acceptable. However, for a high viscosity fluid with a heterogeneous rock pore system with multiple pore type, a combination of 2 MHz and 12 MHz nuclear magnetic frequencies may be needed. In further embodiments, the nuclear magnetic resonance instrument is equipped with variable probes for performing analysis on the samples.

The acoustic analysis of the sample measures frequencies from about 1 Hz to 100,000 MHz. The size of the sample may dictate the frequency. For instance, for an average sized sample, the range may be between 500 KHz to 1 MHz. For a smaller sized sample, higher than 1 MHz may be necessary. Larger sample sizes may require less than 500 MHz.

Various embodiments of this invention will reduce the costs of performing analysis on reservoir samples and will further reduce turnaround time for reservoir evaluation. By perforating multiple analyses together, there will be significant operational benefits of time savings. Additionally, data accuracy will be improved and integration to field and log data will improve. Embodiments of the present invention will provide a comprehensive study platform for EOR and shale gas analysis.

The tri-axial NMR instrument has the capability of performing a number of different tests. Among the tests that could be performed are: NMR test under tri-axial conditions with no pore pressure; NMR test under tri-axial conditions with pore pressure; NMR test under hydrostatic condition with or without pore pressure; NMR test with a combination of tri-axial, hydrostatic, unconfined, pore pressure, acoustic, electrical, temperature, slice NMR, whole NMR, deformation measurement, stress changes (axial, confining, pore), fluids (acoustic, density, electrical measurements), fluid (pressure, volume, temperature, flow rate and components measurements (in flow and out flow)); NMR tests with mechanical tests and combination of sensors; NMR tests with steady state permeability test, tri-axial conditions and sensors for various petro-physical and geo-mechanic data; NMR tests with un-steady state permeability test, tri-axial conditions and sensors for various petro-physical and geo-mechanic data; NMR tests with plate (membrane) capillary pressure test, tri-axial conditions and sensors for various petro-physical and geo-mechanic data; NMR tests for EOR, SAGD, WAG, CO2, chemicals, surfactant, steam, and acid treatments; NMR tests on fluids such as heavy oil, hydrates, asphaltene PPT, and crystallization under hydrostatic conditions; NMR tests with PVT (CCE, Differential liberation), and flow assurance studies under hydrostatic condition.

An exemplary test procedure is described below:
1. Prepare the tri-axial nuclear magnetic resonance apparatus and perform system calibrations.
2. Prepare test specimens.

3. Prepare the NMR instrument setup based on type of test and sample, (i.e., whether the sample is from a core material or a fluid sample).
4. Prepare the correct NMR probe and perform base calibrations.
5. Install the sample into the tri-axial sample holder. Install the tri-axial sample holder in the tri-axial load cell. Install the tri-axial load cell in the NMR apparatus using the ends caps and connect all the feeds for fluids and data sensors.
6. Apply initial axial pressure of about 50 psi (this step could be modified based on sample elastic properties. For example, core samples can be CT-scanned to indicate whether a sample is soft or strings. For stronger samples, the initial pressure may start as high as 1000 psi or higher).
7. Hold the axial displacement and increase confining and pore pressure on the sample until sample has reached test pressures (this step could be different base on sample and test procedures).
8. Circulate temperature control fluid around the tri-axial sample holder and monitor sample temperature and pressure along with other data such as acoustic, strain resistivity, etc.
9. Once the sample has reached required test conditions and all the test parameters are in pseudo equilibrium mode (i.e., within acceptable fluctuations based on specific test parameters), commence the test.
10. During the test, monitor all the sensors, pressures, and test parameters to achieve a successful test conclusion.
11. Unload the samples carefully, bring temperature down to ambient or near ambient temperatures and then slowly reduce the various pressures in a manner so as to maintain sample integrity.

In some embodiments, the present invention provides density, NMR, resistivity, and acoustic measurements of provided and produced fluids as a single phase fluid at reservoir conditions. For instance, in some cases, the fluid is made of a hydrocarbon liquid and gases at a certain pressure and temperature. A drop in either temperature or pressure can convert a single phase fluid into two phases (gas and liquid). Thus, testing of the samples at reservoir conditions allows for more accurate assessment of the mixed gas and liquid samples, as they exist at reservoir conditions. In further embodiments, the present invention also provides density, NMR, resistivity, acoustic and volume measurements of each separated phase (oil, brine, gas, EOR agent), at selected temperature and/or pressure. In further embodiments, the present invention provides measurement of sample deformation as function of stress.

Another use of the tri-axial NMR apparatus will be to integrate the data of the MIR test and measurement to the sonic, resistivity (induction log), gamma and porosity (neutron logs), and geochemical logs. The data may then be extrapolated to wells where samples have not yet been analyzed.

Another use of the tri-axial NMR apparatus relating to fluid analysis is the accurate determination of saturation (bubble point) pressure during a constant composition expansion (CCE) test. The added advantage could be identification of phases, if more than one exists, with the combination of NMR, acoustic measurements, and electrical measurement at the same time. The advantage of doing a CCE test using the tri-axial NMR apparatus as compared to existing methods is that it can provide a time dependent separation and segregation of various fluids based on their densities. Such data can assist in reservoir production close to saturation pressure and for condensate reservoirs analysis.

Although the present invention has been described in detail, it should be understood that various changes, substitutions, and alterations can be made hereupon without departing from the principle and scope of the invention. Accordingly, the scope of the present invention should be determined by the following claims and their appropriate legal equivalents.

The singular forms "a," "an" and "the" include plural referents, unless the context clearly dictates otherwise.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range. Additionally, the ranges should be understood to include all values that are understood by a person of skill in the art as being within the spirit and scope of the invention, including all values that are deemed equivalents, the same, or nearly the same as the particular values being described.

As used herein and in the appended claims, the words "comprise," "has," and "include" and all grammatical variations thereof are each intended to have an open, non-limiting meaning that does not exclude additional elements or steps.

What is claimed is:

1. A tri-axial nuclear magnetic resonance apparatus for testing of petro-physical properties and gathering of geomechanical information, the tri-axial nuclear magnetic resonance apparatus comprising:
   a tri-axial load frame encasing;
      a tri-axial load cell having a tri-axial sample holder and defining at least one pressurizable space surrounding the tri-axial sample holder;
      at least one end cap operable to contact the tri-axial load cell;
      at least one electrical sensor;
      at least one acoustic sensor; and
      a nuclear magnetic resonance instrument located external of the tri-axial load cell; wherein
      the tri-axial load cell is operable to provide a radial pressure of 30,000 psi, an axial pressure of 500,000 psi, a confining pressure of 31,000 psi, and a pore pressure of 30,000 psi.

2. The tri-axial nuclear magnetic resonance apparatus of claim 1, wherein the tri-axial load cell comprises TORLON®.

3. The tri-axial nuclear magnetic resonance apparatus of claim 1, wherein the at least one end cap has pore lines operable to allow for fluid flow.

4. The tri-axial nuclear magnetic resonance apparatus of claim 1, wherein the at least one end cap further comprises a conductor operable for current flow.

5. The hi-axial nuclear magnetic resonance apparatus of claim 1, wherein the at least one end cap further defines one or more cavities for the at least one acoustic sensor.

6. The tri-axial nuclear magnetic resonance apparatus of claim 1, wherein the at least one acoustic sensor is an acoustic transducer operable to analyze variable frequency and mode.

7. The tri-axial nuclear magnetic resonance apparatus of claim 1, wherein the at least one acoustic sensor is operable to function as a transmitter and a receiver.

8. The tri-axial nuclear magnetic resonance apparatus of claim 1, wherein the nuclear magnetic resonance instrument further includes a variable probe.

9. A method for testing of petro-physical properties and gathering of geo-mechanical information, said method comprising the steps of:
 providing a tri-axial nuclear magnetic resonance apparatus, the tri-axial nuclear magnetic resonance apparatus comprising:
  a tri-axial load frame encasing:
   a tri-axial load cell having a tri-axial sample holder and defining at least one pressurizable space surrounding the tri-axial sample holder;
   at least one end cap operable to contact the tri-axial load cell, an axial end of the at least one end cap being in contact with the tri-axial load frame;
   at least one electrical sensor;
   at least one acoustic sensor; and
   a nuclear magnetic resonance instrument located external of the tri-axial load cell; wherein
  the tri-axial load cell is operable to provide an axial pressure that is greater than, and independent of, a confining pressure;
 obtaining a sample from a reservoir,
 loading the tri-axial sample holder in the tri-axial load cell to create a loaded tri-axial load cell;
 placing the loaded tri-axial load cell in contact with the at least one end cap and placing the axial end of the at least one end cap in contact with the tri-axial load frame;
 applying the confining pressure by providing fluid flow through the at least one end cap to the at least one space surrounding the tri-axial sample holder;
 providing a tri-axial pressure including a radial pressure, the axial pressure, the confining pressure and a pore pressure; wherein the tri-axial load cell is operable to provide the radial pressure of 30,000 psi, the axial pressure of 500,000 psi, the confining pressure of 31,000 psi, and the pore pressure of 30,000 psi;
 circulating temperature control fluid around the tri-axial sample holder by providing the temperature control fluid through the at least one end cap to the at least one space surrounding the tri-axial sample holder;
 providing a test fluid through pore lines of the at least one end cap to the tri-axial sample holder;
 performing a time dependent slice nuclear magnetic resonance scan of the sample using the nuclear magnetic resonance instrument to provide nuclear magnetic resonance measurements;
 performing electrical analysis of the sample using the at least one electrical sensor to provide electrical analysis measurements;
 performing acoustic analysis of the sample using the at least one acoustic sensor to provide acoustic measurements; and
 using the nuclear magnetic resonance measurements, the electrical analysis measurements, and acoustic measurements to determine petro-physical properties and geo-mechanical properties of the sample from the reservoir.

10. The method of claim 9, wherein the reservoir is a shale gas reservoir.

11. The method of claim 9, wherein the tri-axial sample holder is maintained at a temperature of between about −20° C. and 350° C.

12. The method of claim 9, wherein the test fluid is a dead fluid.

13. The method of claim 9, wherein the test fluid is a live fluid.

14. The method of claim 9, wherein the nuclear magnetic resonance instrument is operable to function in a frequency range from at least between 0.1 KHz and 20 MHz.

15. The method of claim 9, wherein the at least one acoustic sensor is operable to measure frequencies from 1 Hz to 100,000 MHz.

16. The method of claim 9, wherein the sample is a native sample.

17. The method of claim 9, wherein the sample is a clean sample.

18. The method of claim 9, further comprising the step of performing nuclear magnetic resonance analysis of the sample using a variable probe.

* * * * *